United States Patent
Guerin

(10) Patent No.: US 7,262,244 B2
(45) Date of Patent: *Aug. 28, 2007

(54) POLYMER COMPOSITES COMPRISING LOW MOLECULAR WEIGHT NITRILE RUBBER

(75) Inventor: Frederic Guerin, Petrolia (CA)

(73) Assignee: Lanxess Inc., Sarnia, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 10/684,867

(22) Filed: Oct. 14, 2003

(65) Prior Publication Data

US 2004/0113320 A1 Jun. 17, 2004

(30) Foreign Application Priority Data

Oct. 17, 2002 (CA) .................................. 2409436

(51) Int. Cl.
*C08L 9/02* (2006.01)
*C08F 4/80* (2006.01)

(52) U.S. Cl. .................... 524/565; 524/566; 525/329.1; 525/392.2; 525/329.3; 525/343; 526/171; 526/341

(58) Field of Classification Search ................ 524/565, 524/566; 525/329.1, 329.3, 387, 343; 526/171, 526/341
See application file for complete search history.

(56) References Cited

U.S. PATENT DOCUMENTS

| | | | | |
|---|---|---|---|---|
| 5,002,475 A | * | 3/1991 | Graefe | 425/135 |
| 5,187,232 A | * | 2/1993 | Musch et al. | 525/215 |
| 5,432,226 A | * | 7/1995 | Aonuma et al. | 524/506 |
| 5,651,995 A | * | 7/1997 | Oyama et al. | 524/565 |
| 6,489,385 B1 | * | 12/2002 | Fujii et al. | 524/186 |
| 6,780,939 B2 | * | 8/2004 | Guerin et al. | 525/329.1 |
| 2003/0171518 A1 | | 9/2003 | Magg et al. | 526/297 |
| 2004/0127647 A1 | * | 7/2004 | Ong et al. | 525/191 |
| 2004/0132906 A1 | * | 7/2004 | Guerin et al. | 525/63 |

FOREIGN PATENT DOCUMENTS

| | | |
|---|---|---|
| CA | 2 350 280 | 12/2002 |
| CA | 2 351 961 | 12/2002 |
| CA | 2 357 465 | 3/2003 |
| CA | 2 357 470 | 3/2003 |
| EP | 0 972 797 | 1/2000 |
| WO | WO9736956 A1 * | 10/1997 |

* cited by examiner

*Primary Examiner*—Vasu Jagannathan
*Assistant Examiner*—Vickey Ronesi
(74) *Attorney, Agent, or Firm*—Nicanor A. Kohncke

(57) ABSTRACT

The present invention relates to polymer composites comprising at least one, optionally hydrogenated, nitrile rubber polymer having a Mooney viscosity (ML 1+4 @ 100° C.) below 30 at least one filler and optionally at least one cross-linking agent, a process for preparing said polymer composite wherein at least one, optionally hydrogenated, nitrile rubber polymer having a Mooney viscosity (ML 1+4 @ 100° C.) below 30, at least one filler and optionally at least one cross-linking agent are mixed and a process for the manufacture of a shaped article comprising the step of injection molding a polymer composite comprising at least one, optionally hydrogenated, nitrile rubber polymer having a Mooney viscosity (ML 1+4 @ 100° C.) below 30, at least one filler and at least one cross-linking agent.

11 Claims, No Drawings

POLYMER COMPOSITES COMPRISING LOW MOLECULAR WEIGHT NITRILE RUBBER

FIELD OF THE INVENTION

The present invention relates to polymer composites containing at least one nitrile rubber polymer having a Mooney viscosity (ML 1+4 @ 100° C.) below 30 at least one filler and optionally at least one cross-linking agent, a process for preparing the polymer composite wherein at least one nitrile rubber polymer having a Mooney viscosity (ML 1+4 @ 100° C.) below 30, at least one filler and optionally at least one cross-linking agent are mixed and a process for the manufacture of a shaped article including the step of injection molding a polymer composite containing at least one nitrile rubber polymer having a Mooney viscosity (ML 1+4 @ 100° C.) below 30, at least one filler and at least one cross-linking agent.

BACKGROUND OF THE INVENTION

Hydrogenated nitrile rubber (HNBR), prepared by the selective hydrogenation of acrylonitrile-butadiene rubber (nitrile rubber; NBR, a co-polymer containing at least one conjugated diene, at least one unsaturated nitrile and optionally further comonomers), is a specialty rubber which has very good heat resistance, excellent ozone and chemical resistance, and excellent oil resistance. Coupled with the high level of mechanical properties of the rubber (in particular the high resistance to abrasion) it is not surprising that NBR and HNBR have found widespread use in the automotive (seals, hoses, bearing pads) oil (stators, well head seals, valve plates), electrical (cable sheathing), mechanical engineering (wheels, rollers) and shipbuilding (pipe seals, couplings) industries, among others.

Commercially available HNBR has a Mooney viscosity in the range of from 55 to 105, a molecular weight in the range of from 200,000 to 500,000 g/mol, a polydispersity greater than 3.0 and a residual double bond (RDB) content in the range of from 1 to 18% (by IR spectroscopy).

One limitation in processing HNBR is the relatively high Mooney Viscosity. In principle, HNBR having a lower molecular weight and lower Mooney viscosity would have better processability. Attempts have been made to reduce the molecular weight of the polymer by mastication (mechanical breakdown) and by chemical means (for example, using strong acid), but such methods have the disadvantages that they result in the introduction of functional groups (such as carboxylic acid and ester groups) into the polymer, and the altering of the microstructure of the polymer. This results in disadvantageous changes in the properties of the polymer. In addition, these types of approaches, by their very nature, produce polymers having a broad molecular weight distribution.

A hydrogenated nitrile rubber having a low Mooney (<55) and improved processability, but which has the same microstructure as those rubbers which are currently available, is difficult to manufacture using current technologies. The hydrogenation of NBR to produce HNBR results in an increase in the Mooney viscosity of the raw polymer. This Mooney Increase Ratio (MIR) is generally around 2, depending upon the polymer grade, hydrogenation level and nature of the feedstock. Furthermore, limitations associated with the production of NBR itself dictate the low viscosity range for the HNBR feedstock. Currently, one of the lowest Mooney viscosity products available is Therban® VP KA 8837 (available from Bayer), which has a Mooney viscosity of 55 (ML 1+4 @ 100° C.) and a RDB of 18%.

Co-pending applications CA-2,351,961, CA-2,357,470, CA 2,350,280 and CA 2,357,465 disclose a low-Mooney NBR and HNBR and a method for producing said low-Mooney NBR and HNBR. While the disclosed NBR or HNBR being perfectly suitable for the present invention, said applications are silent about polymer composites comprising said low-Mooney NBR and/or HNBR and methods of producing shaped articles from said low-Mooney NBR and/or HNBR.

SUMMARY OF THE INVENTION

The present invention relates to a polymer composite containing at least one nitrile rubber polymer ("NBR") having a Mooney viscosity (ML 1+4 @ 100° C.) below 30, at least one filler and optionally at least one cross-linking agent. The NBR can be fully or partially hydrogenated ("HNBR"). The present invention also relates to polymer composites containing at least one, optionally hydrogenated, nitrile rubber polymer having a Mooney viscosity (ML 1+4 @ 100° C.) below 20, or, for example, below 10.

The present invention relates to a process for the manufacture of a shaped article including the step of injection molding a polymer composite containing at least one, optionally hydrogenated, nitrile rubber polymer having a Mooney viscosity (ML 1+4 @ 100° C.) below 30, at least one filler and at least one cross-linking agent.

The present invention also relates to a shaped article, such as a seal, hose, bearing pad, stator, well head seal, valve plate, cable sheathing, wheel, roller, pipe seal or footwear component prepared by injection molding and subsequent curing of a polymer composite containing at least one, optionally hydrogenated, nitrile rubber polymer having a Mooney viscosity (ML 1+4 @ 100° C.) below 30, at least one filler and optionally at least one cross-linking agent.

DESCRIPTION OF THE INVENTION

The present invention will now be described for purposes of illustration and not limitation. Except in the operating examples, or where otherwise indicated, all numbers expressing quantities, percentages, and so forth in the specification are to be understood as being modified in all instances by the term "about." Also, all ranges include any combination of the maximum and minimum points disclosed and include any intermediate ranges therein, which may or may not be specifically enumerated herein.

As used throughout this specification, the term "nitrile polymer" or NBR is intended to have a broad meaning and is meant to encompass a copolymer having repeating units derived from at least one conjugated diene, at least one $\alpha,\beta$-unsaturated nitrile and optionally further one or more copolymerizable monomers.

The conjugated diene may be any known conjugated diene, such as a $C_4$-$C_6$ conjugated diene. Useful conjugated dienes include butadiene, isoprene, piperylene, 2,3-dimethyl butadiene and mixtures thereof. For example, the $C_4$-$C_6$ conjugated dienes can be butadiene, isoprene and mixtures thereof. Or for example, the $C_4$-$C_6$ conjugated diene can be butadiene.

The $\alpha,\beta$-unsaturated nitrile may be any known $\alpha,\beta$-unsaturated nitrile, such as a $C_3$-$C_5$ $\alpha,\beta$-unsaturated nitrile. Useful $C_3$-$C_5$ $\alpha,\beta$-unsaturated nitriles include acrylonitrile, methacrylonitrile, ethacrylonitrile and mixtures thereof. For example the $C_3$-$C_5$ $\alpha,\beta$-unsaturated nitrile can be adcrylonitrile.

The copolymer contains in the range of from 40 to 85 weight percent of repeating units derived from one or more conjugated dienes and in the range of from 15 to 60 weight percent of repeating units derived from one or more unsaturated nitrites. For example, the copolymer contains in the range of from 60 to 75 weight percent of repeating units derived from one or more conjugated dienes and in the range of from 25 to 40 weight percent of repeating units derived from one or more unsaturated nitrites. Or further, for example, the copolymer contains in the range of from 60 to 70 weight percent of repeating units derived from one or more conjugated dienes and in the range of from 30 to 40 weight percent of repeating units derived from one or more unsaturated nitrites.

Optionally, the copolymer may further contain repeating units derived from one or more copolymerizable monomers, such as unsaturated carboxylic acids. Non-limiting examples of suitable unsaturated carboxylic acids are fumaric acid, maleic acid, acrylic acid, methacrylic acid and mixtures thereof. Repeating units derived from one or more copolymerizable monomers will replace a portion of either the nitrile or the diene monomers of the nitrile rubber and it will be apparent to the skilled in the art that the above mentioned figures will have to be adjusted to result in 100 weight percent. In case of the mentioned unsaturated carboxylic acids, the nitrile rubber can contain repeating units derived from one or more unsaturated carboxylic acids in the range of from 1 to 10 weight percent of the rubber, with this amount displacing a portion of the corresponding amount of the conjugated diolefin.

Other preferred optionally further monomers are unsaturated mono- or di-carboxylic acids or derivatives thereof (e.g., esters, amides and the like) including mixtures thereof.

Hydrogenated in the present invention is understood to mean more than 50% of the residual double bonds (RDB) present in the starting nitrile polymer/NBR are hydrogenated, for example, more than 90% of the RDB are hydrogenated, further for example, more than 95% of the RDB are hydrogenated or for example, more than 99% of the RDB are hydrogenated.

The Mooney viscosity of the rubber was determined using ASTM test D1646.

The polymer composite according to the present invention contains at least one, optionally hydrogenated, NBR having a Mooney viscosity (ML 1+4 @ 100° C. according to ASTM test D1646) of less than 30, for example, less than 20, further for example, less than 15 and even further for example, less than 10.

According to the present invention, the low-Mooney, optionally hydrogenated NBR can have a polydispersity index of less than 3, or for example, less than 2.9, or less than 2.8, or less than 2.7, or less than 2.6, of for example, less than 2.5, or less than 2.4, or less than 2.3, or less than 2.2.

The present invention is not restricted to a special process for preparing the optionally hydrogenated NBR. However, the NBR/HNBR of the present invention is readily available in a two step synthesis as disclosed in CA-2,351,961, CA-2,357,470, CA 2,350,280 and CA 2,357,465, which may take place in the same reaction set-up or different reactors. For jurisdictions allowing for this procedure, CA-2,351,961, CA-2,357,470, CA 2,350,280 and CA 2,357,465 are incorporated herein by reference.

Step 1: Metathesis

The metathesis reaction is conducted in the presence of one or more compounds of the general formulas I, II, III or IV;

Formula I wherein:

M is Os or Ru,

R and $R^1$ are, independently, hydrogen or a hydrocarbon selected from the group consisting of $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, X and $X^1$ are independently any anionic ligand, and L and $L^1$ are independently any neutral ligand, such as phosphines, amines, thioethers or imidazolidinylidenes or any neutral carbene, optionally, L and $L^1$ can be linked to one another to from a bidentate neutral ligand;

Formula II wherein:

$M^1$ is Os or Ru;

$R^2$ and $R^3$ are, independently, hydrogen or a hydrocarbon selected from the group consisting of $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, $X^2$ is a anionic ligand, and $L^2$ is a neutral π-bonded ligand, independent of whether they are mono- or polycyclic, $L^3$ is a ligand selected from phosphines, sulfonated phosphines, fluorinated phosphines, functionalized phosphines bearing up to three aminoalkyl-, ammoniumalkyl-, alkoxyalkyl-, alkoxylcarbonylalkyl-, hydrocycarbonylalkyl-, hydroxyalkyl- or ketoalkyl-groups, phosphites, phosphinites, phosphonites, phosphinamines, arsines, stibenes, ethers, amines, amides, imines, sulfoxides, thioethers and pyridines, $Y^-$ is a non-coordinating anion, n is an integer in the range of from 0 to 5;

Formula III wherein $M^2$ is Mo or W, $R^4$ and $R^5$ are, independently, hydrogen or a hydrocarbon selected from the group consisting of $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, $R^6$ and $R^7$ are independently selected from any unsubstituted or halo-substitutrd alkyl, aryl, aralkyl groups or silicon-containing analogs thereof, Formula VI

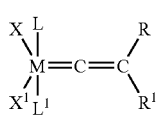

wherein:

M is Os or Ru,

R and $R^1$ are independently selected from the group consisting of hydrogen, substituted or unsubstituted alkyl, and substituted or unsubstituted alkyl, X and $X^1$ are independently any anionic ligand, and L and $L^1$ are independently any neutral ligand, such as phosphines, amines, thioethers or imidazolidinylidenes or any neutral carbene, optionally, L and $L^1$ can be linked to one another to from a bidentate neutral ligand;

For example, the compound can be according to Formula I. Further for example, the compound can be according to Formula I wherein L and $L^1$ are trialkylphosphines, X and $X^1$ are chloride ions and M is Ruthenium.

The amount of compounds will depend upon the nature and catalytic activity of the compound(s) in question. Typically, the ratio of compound(s) to NBR is in the range of from 0.005 to 5, or for example in the range of from 0.025 to 1 and, also for example, in the range of from 0.1 to 0.5.

The metathesis reaction can be carried out in the presence of a co-olefin such as a $C_2$ to $C_{16}$ linear or branched olefin such as ethylene, isobutene, styrene or 1-hexene. Where the co-olefin is a liquid (such as 1-hexene), the amount of co-olefin employed can be in the range of from 1 to 200 weight %. Where the co-olefin is a gas (such as ethylene) the amount of co-olefin employed is such that it results in a pressure in the reaction vessel in the range of from $1*10^5$ Pa to $1*10^7$ Pa, of for example, in the range of from $5.2*10^5$ Pa to $4*10^6$ Pa.

The metathesis reaction can be carried out in any suitable solvent which does not inactivate the catalyst or otherwise interfere with the reaction. Useful solvents include, but are not limited to, dichloromethane, benzene, toluene, tetrahydrofuran, cylcohexane and the like. For example, the solvent can be monochlorobenzene (MCB). In certain cases the co-olefin can itself act as a solvent (for example, 1-hexene), in which case no other solvent is necessary.

The concentration of nitrile polymer (NBR) in the reaction mixture is not critical but, should be such that the reaction is not hampered if the mixture is too viscous to be stirred efficiently. For example, the concentration of NBR is in the range of from 1 to 20% by weight, or in the range of from 6 to 15% by weight.

The metathesis reaction can be carried out at a temperature in the range of from 20 to 140° C.; or in the range of from 60 to 120° C.

The reaction time will depend upon a number of factors, including cement concentration, amount of catalyst used and the temperature at which the reaction is performed. The metathesis is usually complete within the first two hours under typical conditions. The progress of the metathesis reaction may be monitored by standard analytical techniques, for example using GPC or solution viscosity. Whenever referenced throughout the specification the molecular weight distribution of the polymer was determined by gel permeation chromatography (GPC) using a Waters 2690 Separation Module and a Waters 410 Differential Refractometer running Waters Millenium software version 3.05.01. Samples were dissolved in tetrahydrofuran (THF) stabilized with 0.025% BHT. The columns used for the determination were three sequential mixed-B gel columns from Polymer Labs. Reference Standards used were polystyrene standards from American Polymer Standards Corp.

Step 2: Hydrogenation

After the metathesis reaction, the nitrile polymer must be hydrogenated to result in a partially or fully hydrogenated nitrile polymer (HNBR). HNBR are preferred useful in the present invention. Reduction of the product from the metathesis reaction can be effected using standard reduction techniques known in the art. For example, homogeneous hydrogenation catalysts known to those of skill in the art, such as Wilkinson's catalyst $\{(PPh_3)_3RhCl\}$ and the like can be used.

The hydrogenation may be performed in situ i.e. in the same reaction vessel in which the metathesis step is carried out, without the need to first isolate the metathesised product. The hydrogenation catalyst is simply added to the vessel, which is then treated with hydrogen to produce the HNBR.

Grubb's catalyst, in the presence of hydrogen, is converted to a dihydride complex $(PR_3)_2RUCl_2H_2$, which is itself an olefin hydrogenation catalyst. Thus, in a favorable one-pot reaction, Grubb's catalyst was used to reduce the molecular weight of NBR in the presence of co-olefin. The reaction mixture is then treated with hydrogen, converting the Grubb's complex to the dihydride species which then hydrogenated the metathesis product to produce the HNBR according to the present invention. The rate of hydrogenation was lower in this case than in the case where Wilkinson's catalyst was used for the hydrogenation step, but it is clear that such an approach is indeed a viable one.

The low Mooney NBR as well as the low Mooney HNBR which forms a preferred component of the polymer composite of the invention can be characterized by standard techniques known in the art. For example, the molecular weight distribution of the polymer was determined by gel permeation chromatography (GPC) using a Waters 2690 Separation Module and a Waters 410 Differential Refractometer running Waters Millennium software version 3.05.01. Samples were dissolved in tetrahydrofuran (THF) stabilized with 0.025% BHT. The columns used for the determination were three sequential mixed-B gel columns from Polymer Labs. Reference Standards used were polystyrene standards from American Polymer Standards Corp.

The present inventive polymer composite further may contain at least one filler. The filler may be an active or an inactive filler or a mixture thereof. The filler may be, for example:

highly dispersed silicas, prepared e.g. by the precipitation of silicate solutions or the flame hydrolysis of silicon halides, with specific surface areas of in the range of from 5 to 1000 m²/g, and with primary particle sizes of in the range of from 10 to 400 nm; the silicas can optionally also be present as mixed oxides with other metal oxides such as those of Al, Mg, Ca, Ba, Zn, Zr and Ti;

synthetic silicates, such as aluminum silicate and alkaline earth metal silicate like magnesium silicate or calcium silicate, with BET specific surface areas in the range of from 20 to 400 m²/g and primary particle diameters in the range of from 10 to 400 nm;

natural silicates, such as kaolin and other naturally occurring silica;

glass fibers and glass fiber products (matting, extrudates) or glass microspheres;

metal oxides, such as zinc oxide, calcium oxide, magnesium oxide and aluminum oxide;

metal carbonates, such as magnesium carbonate, calcium carbonate and zinc carbonate;

metal hydroxides, e.g. aluminum hydroxide and magnesium hydroxide;

carbon blacks; the carbon blacks to be used here are prepared by the lamp black, furnace black or gas black process and have preferably BET (DIN 66 131) specific surface areas in the range of from 20 to 200 m²/g, e.g. SAF, ISAF, HAF, FEF or GPF carbon blacks;

rubber gels, especially those based on polybutadiene, butadiene/styrene copolymers, butadiene/acrylonitrile copolymers and polychloroprene; or mixtures thereof.

Examples of preferred mineral fillers include silica, silicates, clay such as bentonite, gypsum, alumina, titanium dioxide, talc, mixtures of these, and the like. These mineral particles have hydroxyl groups on their surface, rendering them hydrophilic and oleophobic. This exacerbates the difficulty of achieving good interaction between the filler particles and the rubber. For many purposes, the mineral is silica, such as silica made by carbon dioxide precipitation of sodium silicate. Dried amorphous silica particles suitable for use in accordance with the invention may have a mean agglomerate particle size in the range of from 1 to 100 microns, or for example between 10 and 50 microns and further for example between 10 and 25 microns. According to the present invention, for example, less than 10 percent by volume of the agglomerate particles are below 5 microns or over 50 microns in size. A suitable amorphous dried silica moreover usually has a BET surface area, measured in accordance with DIN (Deutsche Industrie Norm) 66131, of in the range of from 50 and 450 square meters per gram and a DBP absorption, as measured in accordance with DIN 53601, of in the range of from 150 and 400 grams per 100 grams of silica, and a drying loss, as measured according to DIN ISO 787/11, of in the range of from 0 to 10 percent by weight. Suitable silica fillers are available under the trademarks HiSil® 210, HiSil® 233 and HiSil® 243 from PPG Industries Inc. Also suitable are Vulkasil S and Vulkasil N, from Bayer AG.

Often, use of carbon black as a filler is advantageous. Usually, carbon black is present in the polymer composite in an amount of in the range of from 20 to 200 parts by weight, or for example from 30 to 150 parts by weight, or further for example from 40 to 100 parts by weight. Further, it might be advantageous to use a combination of carbon black and mineral filler in the present inventive polymer composite. In this combination the ratio of mineral fillers to carbon black is usually in the range of from 0.05 to 20, or for example 0.1 to 10.

The polymer composite may advantageously further contain other natural or synthetic rubbers such as BR (polybutadiene), ABR (butadiene/acrylic acid-$C_1$-$C_4$-alkylester-copolymers), CR (polychloroprene), IR (polyisoprene), SBR (styrene/butadiene-copolymers) with styrene contents in the range of 1 to 60 wt %, NBR (butadiene/acrylonitrile-copolymers with acrylonitrile contents of 5 to 60 wt %, HNBR with a Mooney viscosity (ML 1+4 @ 100° C. according to ASTM test D1646) of at least 30 (partially or totally hydrogenated NBR-rubber), EPDM (ethylene/propylene/diene-copolymers), FKM (fluoropolymers or fluororubbers), and mixtures of the given polymers. Careful blending with conventional HNBR often reduces cost of the polymer composite without sacrificing the processability. The amount of conventional HNBR and/or other natural or synthetic rubbers will depend on the process condition to be applied during manufacture of shaped articles and is readily available by few preliminary experiments.

The polymer composite furthermore optionally comprises one or more cross-linking agents or curing systems. The invention is not limited to a special curing system, suitable curing systems include sulfur and peroxide curing systems, peroxide curing system are preferred. Furthermore, the invention is not limited to a special peroxide curing system. For example, inorganic or organic peroxides are suitable. For example, organic peroxides such as dialkylperoxides, ketaiperoxides, aralkylperoxides, peroxide ethers, peroxide esters, such as di-tert.-butylperoxide, bis-(tert.-bulylperoxy-lsopropyl)-benzene, dicumylperoxide, 2.5-dimethyl-2,5-di (tert.-butylperoxy)-hexane, 2,5-dimethyl-2,5-di(tert-butylperoxy)-hexene-(3), 1,1-bis-(tert.-butylperoxy)-3,3,5-trimethyl-cyclohexane, benzoylperoxide, tert.-butylcumylperoxide and tert.-butylperbenzoate are useful in the present invention. Usually the amount of peroxide in the polymer composite is in the range of from 1 to 10 phr (=per hundred rubber), or for example, from 4 to 8 phr. Subsequent curing is usually performed at a temperature in the range of from 100 to 200° C., or for example, 130 to 180° C. Peroxides might be applied advantageously in a polymer-bound form. Suitable systems are commercially available, such as Polydispersion T(VC) D-40 P from Rhein Chemie Rhsinau GmbH, D (polymerbound di-tert.-butylperoxy-isopropylbenzene).

The rubber composition according to the present invention can contain further auxiliary products for rubbers, such as reaction accelerators, vulcanizing accelerators, vulcanizing acceleration auxiliaries, antioxidants, foaming agents, anti-aging agents, heat stabilizers, light stabilizers, ozone stabilizers, processing aids, plasticizers, tackifiers, blowing agents, dyestuffs, pigments, waxes, extenders, organic acids, inhibitors, metal oxides, and activators such as triethanolamine, polyethylene glycol, hexanetriol, etc., which are known to the rubber industry. The rubber aids are used in conventional amounts, which depend inter alia on the intended use. Conventional amounts are e.g. from 0.1 to 50 wt. %, based on rubber. According to the present invention, the composition can contain in the range of 0.1 to 20 phr of an organic fatty acid as an auxiliary product, such as a unsaturated fatty acid having one, two or more carbon double bonds in the molecule which more preferably includes 10% by weight or more of a conjugated diene acid having at least one conjugated carbon-carbon double bond in its molecule. Those fatty acids can have in the range of from 8-22 carbon atoms, or for example from 12-18. Examples include stearic acid, palmitic acid and oleic acid and their calcium-, zinc-, magnesium-, potassium- and ammonium salts. According to the present invention, the composition can contain in the range of 5 to 50 phr of an acrylate as an auxiliary product. Suitable acrylates are known from EP-A1-0 319 320, in particular p. 3, I. 16 to 35, from U.S. Pat. No. 5,208,294, in particular Col. 2, I. 25 to 40, and from U.S. Pat. No. 4,983,678, in particular Col. 2, I. 45 to 62. Reference is made to zinc acrylate, zinc diacrylate or zinc dimethacrylate or a liquid acrylate, such as trimethylolpropane-trimethacrylate (TRIM), butanedioldimethacrylate (BDMA) and ethylenglycoldimethacrylate (EDMA). It might be advantageous to use a combination of different acrylates and/or metal salts thereof. It may also be advantageous to use metal acrylates in combination with a Scorch-retarder such as sterically hindered phenols (e.g. methyl-substituted aminoalkylphenols, such as 2,6-di-tert.-butyl-4-dimethylaminomethylphenol).

The ingredients of the polymer composite are mixed together, suitably at an elevated temperature that may range from 25° C. to 200° C. Normally the mixing time does not exceed one hour and a time in the range from 2 to 30 minutes is usually adequate. The mixing is suitably carried out in an internal mixer such as a Banbury mixer, or a Haake or Brabender miniature internal mixer. A two roll mill mixer also provides a good dispersion of the additives within the elastomer. An extruder also provides good mixing, and permits shorter mixing times. It is possible to carry out the mixing in two or more stages, and the mixing can be done in different apparatus, for example one stage in an internal mixer and one stage in an extruder. However, it should be taken care that no unwanted pre-crosslinking (scorch) occurs during the mixing stage. For compounding and vulcanization see also: Encyclopedia of Polymer Science and Engineering, Vol. 4, p. 66 et seq. (Compounding) and Vol. 17, p. 666 et seq. (Vulcanization).

Due to the low viscosity of the polymer composite, the polymer composite is ideally suited to be processed by but not limited to molding injection technology. The polymer composite can also be useful to transfer molding, to compression molding, to liquid injection molding. The polymer composite containing a cross-linking system is usually introduced in a conventional injection molding and injected into hot (about 160-230° C.) forms where the cross-linking/vulcanization takes place depending on the polymer composite composition and temperature of the mold.

The inventive polymer composite is very well suited for the manufacture of a shaped article, such as a seal, hose, bearing pad, stator, well head seal, valve plate, cable sheathing, wheel, roller, pipe seal, in place gaskets or footwear component prepared by injection molding technology.

EXAMPLES

Example 1

Bis(tricyclohexylphosphine)benzylidene ruthenium dichloride (Grubb's metathesis catalyst), 1-hexene and monochlorobenzene (MCB) were purchased from Alfa, Aldrich Chemicals, and PPG respectively and used as received. Perbunan was obtained from Bayer Inc.

The metathesis reactions were carried out in a pilot size reactor under the following conditions:

| | |
|---|---|
| Cement Concentration | 6% |
| Co-Olefin | Ethylene |
| Co-Olefin Concentration | 500 psi |
| Agitator Speed | 600 rpm |
| Reactor Temperature | 80° C. |
| Catalyst Loading | 0.25 phr |

-continued

| | |
|---|---|
| Solvent | Monochlorobenzene |
| Substrate | statistical Butadiene-acrylonitrilecopolymer with a acrylonitrile content of 34 mol % and a Mooney-Viscosity ML (1 + 4) @ 100 deg. C. of 35 |

The polymer (9 kg) was dissolved in monochlorobenzene (141 kg). The reactor was heated to desired temperature and 2 L of a monochlorobenzene solution containing Grubb's catalyst was added to the reactor. The reactor was pressurized with ethylene to a pressure of 500 psi. The temperature was maintained constant for the duration of the reaction. A cooling coil connected to a temperature controller and a thermal sensor was used to regulate the temperature. The progress of the reaction was monitored using solution viscosity measurements for the 6% cements.

The hydrogenation reactions were carried out in the same reactor as the metathesis under the following conditions:

| | |
|---|---|
| Cement solid concentration | 6% |
| $H_2$(g) pressure | 1200 psi |
| Agitator Speed | 600 rpm |
| Reactor Temperature | 138° C. |
| Catalyst Loading (Wilkinson's) | 0.075 phr |
| Triphenylphosphine | 1 phr |
| Solvent | Monochlorobenzene |

The cement from the metathesis reaction was degassed 3 times with $H_2$ (100 psi) under full agitation. The temperature of the reactor was raised to 130° C. and a 1 L monochlorobenzene solution containing Wilkinson's catalyst and triphenylphosphine was added to the reactor. The temperature was allowed to increase to 138° C. and maintained constant for the duration of the reaction. The hydrogenation reaction was monitored by measuring the residual double bond (RDB) level at various intervals using IR spectroscopy.

Alternatively, the Ruthenium metathesis catalyst could be used to hydrogenate the polymer.

Examples 2-6

Compounding and Physical Testing

Polymer composites were mixed on an open mill. The curatives were added on a cold open mill in a separate mixing step. The formulations used in this assessment are based on a simplified peroxide recipe according to Table 1.

Carbon black N 660 Sterling-V available from Cabot Tire Blacks

Maglite® D is a MgO available from C. P. Hall.

Naugard® 445 is a diphenylamine available from Uniroyal Chemical.

Plasthall TOTM is a Trioctyl trimellitate available from C. P. Hall.

Vulkanox® ZMB-2/C5 is a Zinc salt of 4- and 5-methyl-mercapto benzimidazole available from Bayer AG DIAK #7 is a Triallylisocyanurate available from DuPont Dow Elastomers Vulcup 40KE is 2,2'-bis (tert-butylperoxy di-isopropyl-benzene) available from Harwick Standard.

TABLE 1

Compounding Recipe

| Experiment | 2 (comp.) | 3 | 4 | 5 | 6 (comp.) |
|---|---|---|---|---|---|
| Therban ® A3407 | 100 | | | | 100 |
| HNBR of Example 1 | | 100 | 100 | 100 | |
| Carbon Black, N 660 Sterling-V | 50 | 50 | 50 | 50 | 50 |
| Maglite ® D | 3 | 3 | 3 | 3 | 3 |
| Naugard ® 445 | 1 | 1 | 1 | 1 | 1 |
| Plasthall TOTM | 5 | | | | |
| Vulkanox ® ZMB-2/C5 (ZMMBI) | 0.4 | 0.4 | 0.4 | 0.4 | 0.4 |
| Zinc Oxide (Kadox ® 920) Grade PC 216 | 3 | 3 | 3 | 3 | 3 |
| Curatives | | | | | |
| DIAK #7 | 1.5 | 2 | 2.4 | 2.8 | 1.5 |
| Vulcup 40KE | 7.5 | 10 | 12 | 14 | 7.5 |

Polymer Properties

A summary of the raw polymer properties is shown in Table 2. The molecular weight (Mw) of the Polymer of Example 1 is ¼ that of regular Therban® A3407 while the narrow polydispersity (PDI) is 2.1 compared to 3.2 for the regular grade.

TABLE 2

Summary of Raw Polymer Properties

| | Mn | Mw | PDI | ML 1 + 4 @ 100° C. |
|---|---|---|---|---|
| Polymer from Exp. 1 | 37000 | 76000 | 2.1 | 6.5 |
| Therban ® A3407 | 97000 | 314000 | 3.2 | 70.5 |

Polymer Composites Properties

Table 3 shows a summary of the properties of polymer composites of Exp. 2-6. Examples 2 and 6 are for comparison.

TABLE 3

Summary of Polymer Composites Properties

| | Example | | | | |
|---|---|---|---|---|---|
| | 2 | 3 | 4 | 5 | 6 |
| Mooney ML 1 + 4 @ 100° C. | | | | | |
| Raw Polymer | 70 | | 6.5 | | 70 |
| Polymer composite | 91.0 | 16.8 | 16.0 | 15.4 | 107.8 |
| MH (dN.m) | 51.4 | 37.5 | 50.5 | 62.6 | 58.7 |
| ML (dN.m) | 3.1 | 0.1 | 0.1 | 0.1 | 3.8 |
| Delta Torque (dN.m) | 48.3 | 37.4 | 50.4 | 62.5 | 54.6 |
| t90 (minutes) | 13.7 | 16.7 | 15.8 | 14.6 | 13.7 |
| 100% Modulus (Mpa) | 7.8 | 9.3 | 13.3 | 17.9 | 9.2 |
| Ultimate Tensile (Mpa) | 23.3 | 19.5 | 19.3 | 18.4 | 25.6 |
| Elongation at Break (%) | 211 | 172 | 132 | 102 | 202 |
| Hardness Shore A | 68 | 69 | 71 | 73 | 70 |
| Compression Set in % after 168 h @ 150° C. | 20.14 | 22.85 | 21.69 | 20.67 | 22.54 |
| DIN Abrasion | 86 | 125 | 126 | 124 | 76 |
| Heat Rise (° C.) | 28 | 32 | 27 | 24 | 29 |
| Permanent Set (%) | 0.7 | 0.4 | 0.3 | 0.2 | 0.4 |

From Table 3, it is clear that although the molecular weight (Mw) of the Low Mooney HNBR used in polymer composites 2-5 is only ¼ that of Therban® A3407, the physical properties remain very good. The excellent physical properties of such a low molecular weight polymer might be attributed to the narrow molecular weight distribution. The low molecular weight and the narrow MWD result in a favorable viscosity which allows for injection molding processes for producing shaped articles.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A polymer composite comprising at least one, optionally hydrogenated, nitrile rubber polymer having a Mooney viscosity (ML 1+4 @ 100° C.) below 30 and a polydispersity below 2.7 at least one filler and optionally at least one cross-linking agent, wherein the optionally hydrogenated, nitrile rubber polymer is prepared by reacting a nitrile polymer in the presence of one ore more compounds of the general formulas I, II, III or IV;

Formula I wherein:

M is Os or Ru,

R and $R^1$ are, independently, hydrogen or a hydrocarbon selected from the group consisting of $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, X and $X^1$ are independently any anionic ligand, and L and $L^1$ are independently any neutral ligand;

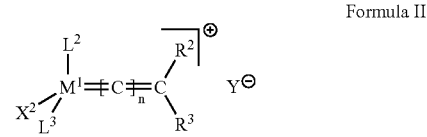

Formula II wherein:

$M^1$ is Os or Ru;

$R^2$ and $R^3$ are, independently, hydrogen or a hydrocarbon selected from the group consisting of $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, $C_2$-$C_{20}$ alkynyloxy, aryloxy, $C_2$-$C_{20}$ alkoxycarbonyl, $C_1$-$C_{20}$ alkylthio, $C_1$-$C_{20}$ alkylsulfonyl and $C_1$-$C_{20}$ alkylsulfinyl, $X^2$ is an anionic ligand, and $L^2$ is a neutral π-bonded ligand, independent of whether it is mono- or polycyclic, $L^3$ is a ligand selected from the group consisting of phosphines, sulfonated phosphines, fluorinated phosphines, functionalized phosphines bearing up to three aminoalkyl-, ammoniumalkyl-, alkoxyalkyl-, alkoxylcarbonylalkyl-, hydrocycarbonylalkyl-, hydroxyalkyl- or ketoalkyl- groups, phosphites, phosphinites, phosphonites, phosphinamines, arsines, stibenes, ethers, amines, amides, imines, sulfoxides, thioethers and pyridines, Y' is a non-coordinating anion,
n is an integer in the range of from 0 to 5;

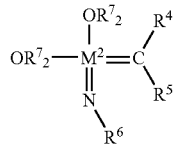

Formula III wherein
$M^2$ is Mo or W,
$R^4$ and $R^5$ are, independently, hydrogen or a hydrocarbon selected from the group consisting of $C_2$-$C_{20}$ alkenyl, $C_2$-$C_{20}$ alkynyl, $C_1$-$C_{20}$ alkyl, aryl, $C_1$-$C_{20}$ carboxylate, $C_1$-$C_{20}$ alkoxy, $C_2$-$C_{20}$ alkenyloxy, C2-$C_{20}$ alkynyloxy, aryloxy, $C_2$-$C_{20}$ alkoxycarbonyl, $C_1$-$C_{20}$ alkythio, $C_1$-$C_{20}$ alkylsulfonyl and $C_1$-$C_{20}$ alkylsulfinyl,
$R^6$ and $R^7$ are independently selected from any unsubstituted or halo-substituted alkyl, aryl, aralkyl groups or silicon-containing analogs thereof,

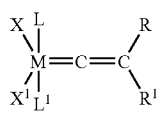

Formula VI wherein:
M is Os or Ru,
R and $R^1$ are independently selected from the group consisting of hydrogen, substituted or unsubstituted alkyl, and substituted or unsubstituted alkyl,
X and $X^1$ are independently any anionic ligand, and
L and $L^1$ are independently any neutral ligand.

2. The polymer composite according to claim 1, wherein the polymer Mooney viscosity (ML 1+4 @ 100° C.) is below 20.

3. The polymer composite according to claim 1, wherein the polymer Mooney viscosity (ML 1+4 @ 100° C.) is below 10.

4. The polymer composite according to claim 1, wherein the polymer composite further comprises a curing system selected from the group consisting of peroxide curing systems and sulfur curing systems.

5. A process for preparing the polymer composite according to claim 1, comprising mixing at least one, optionally hydrogenated, nitrile rubber polymer having a Mooney viscosity (ML 1+4 @ 100° C.) below 30, at least one filler and optionally at least one cross-linking agent.

6. A process for the manufacture of a shaped article comprising the step of injection molding the polymer composite according to claim 1, comprising at least one, optionally hydrogenated, nitrile rubber polymer having a Mooney viscosity (ML 1+4 @ 100° C.) below 30 and a polydispersity index below 2.7, at least one filler and at least one cross-linking agent.

7. A process according to claim 6, wherein the shaped article is seal, gasket, belt, hose, bearing pad, stator, well head seal, valve plate, cable sheathing, wheel, roller, in place gaskets or pipe seal.

8. The process for the manufacture of a shaped article comprising the step of liquid injection molding the polymer composite according to claim 1, comprising at least one, optionally hydrogenated, nitrite rubber polymer having a Mooney viscosity (ML 1+4 @ 100° C.) below 10, at least one filler and at least one cross-linking agent.

9. The process according to claim 8, wherein the shaped article is seal, gasket, belt, hose, bearing pad, stator, well head seal, valve plate. cable sheathing, wheel, roller, in place gaskets or pipe seal.

10. The process according to claim 1, wherein natural ligands L and $L^1$ are selected from the group consisting of phosphines, amines, thioethers, imidazolidinylidenes and any neutral carbine.

11. The process according to claim 1, wherein L and $L^1$ are linked to one another to from a bidentate neutral ligand.

* * * * *